United States Patent [19]

Meeten

[11] Patent Number: 5,546,791
[45] Date of Patent: Aug. 20, 1996

[54] RHEOMETER

[75] Inventor: Gerald H. Meeten, Ware, England

[73] Assignee: Schlumberger Technology Corporation, Houston, Tex.

[21] Appl. No.: 375,062

[22] Filed: Jan. 19, 1995

Related U.S. Application Data

[63] Continuation of Ser. No. 66,121, filed as PCT/GB91/02139, Dec. 3, 1991, published as WO92/10736, Jun. 25, 1992, abandoned.

[30] Foreign Application Priority Data

Dec. 4, 1990 [GB] United Kingdom .................. 9026294

[51] Int. Cl.⁶ .................................................. G01N 11/14
[52] U.S. Cl. ........................................ 73/54.28; 73/54.32
[58] Field of Search ............................... 73/54.02, 54.03, 73/54.23, 54.28, 54.32, 54.34, 54.38, 54.35, 64.56

[56] References Cited

U.S. PATENT DOCUMENTS

| | | | |
|---|---|---|---|
| 2,846,873 | 8/1958 | Külle | 73/54.28 |
| 3,611,789 | 10/1971 | Lopas | 73/54.28 |
| 3,777,551 | 12/1973 | Weiss | 73/54.28 |
| 4,175,425 | 11/1979 | Brookfield | 73/54.28 |
| 4,430,889 | 2/1984 | Sutton | 73/147 |
| 4,501,155 | 2/1985 | Garritano | 73/847 |
| 4,534,210 | 8/1985 | Reeves | 73/54.32 |
| 4,557,142 | 12/1985 | Hensley et al. | 73/153 |
| 4,612,800 | 9/1986 | Erian | 73/54.01 |
| 4,653,313 | 3/1987 | Sabins et al. | 73/54.39 |
| 4,817,416 | 4/1989 | Blanch et al. | 73/54.04 |

FOREIGN PATENT DOCUMENTS

| | | |
|---|---|---|
| 1270378 | 6/1990 | Canada. |
| 219913 | 4/1987 | European Pat. Off.. |
| 274279 | 12/1989 | German Dem. Rep.. |
| 1242757 | 7/1986 | U.S.S.R. ................................. 73/54.28 |

OTHER PUBLICATIONS

Shah and Sutton, "New Friction Correlation for Cements from Pipe and Rotational Viscometer Data", SPE 19539, Oct. 8–11, 1989. San Antonio, Texas, USA.

Newman FH and Searle VHL "The general properties of matter", 5th edition, pp. 226–227, London, England.

Knoll SK "Wall slip evaluation in steady shear viscosity measurements of hydraulic fracturing fluids", SPE/DOE 13904, May 19–22, 1985, Denver, Colorado, USA.

Blaszczyk J and Petela R "Application of a modified rotary rheometer to the investigation of slurries", Rheologica Acta, 25:521–526 (1986).

Primary Examiner—Hezron E. Williams
Assistant Examiner—Michael J. Brock
Attorney, Agent, or Firm—Wayne I. Kanak; Martin D. Hyden; Leonard W. Pojunas

[57] ABSTRACT

There is provided a rheometer, comprising a cup for a fluid to be measured, a concentric rotor and stator arrangement, and a circuit for circulating the fluid which includes a pump for providing in pulsatile, non-laminar flow in the cup. By using the pump to provide both a turbulent and pulsating flow, particulate matter can be maintained in suspension and flow induced through the measuring system while any rheology effect the pumping system has on the fluid is introduced independently of rheology effects caused by the measuring system itself. Thus the pumping can be continued while the measurement is being made.

13 Claims, 6 Drawing Sheets

5,546,791

RHEOMETER

This application is a file wrapper continuation of parent application Ser. No. 08/066,121, filed as PCT/GB91/02139, Dec. 3, 1991 published as WO92/10736, Jun. 25, 1992, now abandoned.

BACKGROUND OF THE INVENTION

1. Field of the Invention

The present invention relates to a rheometer which is suitable for use with fluids containing materials dispersed therein.

2. Description of the Prior Art

The theology of thixotropic or granular fluid slurries such as cement slurries or drilling mud can be useful for determining the behaviour of the material in use. The current standard rheology measurement specified by the American Petroleum Industry (API) utilizes a rheometer comprising a cup for holding a sample to be tested and a rotor/stator arrangement which can be positioned in the sample in the cup. The rotor/stator arrangement comprises a cylindrical driven rotor having a vaned stator mounted coaxially therein on the rotation axis. In use, rotation of the rotor causes a torque to be applied to the stator and a comparison of the rate of rotation and torque can be used to determine the properties of the sample.

It has been observed that rheometers of this general type do suffer from problems which affect the accuracy of the results obtained. In the API specified geometry the effects which can be encountered are: end effects, slippage at the wall and particle migration. End effects arise from the torque generated by flow from the ends of the concentric cylinders comprising the rotor/stator arrangement and may cause the shear stress calculated from the rheometer reading to be under estimated by up to 10%. Slippage at the wall occurs when fluids having a dispersed particulate phase become depleted in solids near the solid walls of the rheometer. This in turn reduces the viscosity and hence yield stress. Slippage is mainly evident at low shear rates (less than 20 s$^{-1}$) and is less important at higher shear rates. Particle migration can be caused by two main effects: gravity and centrifugation. The effect of gravity is to reduce the particle content where the rheology is measured and the effect is greater for sheared samples. Furthermore, the build-up of solids below the rotor/stator can cause extra torque to be transmitted to the stator giving greater error. Centrifugation is particularly apparent in the external rotor arrangement specified by API and causes a build up of particles in the inside of the rotor and has the effect of increasing the torque measured.

Various attempts have previously been made to reduce one or more of the effects outlined above. These attempts include the provision of a pump and baffle arrangement for example as described in SPE Paper Production Engineering, November 1990, pp 415–424 by Shah and Sutton, the provision of slots at the upper end of the rotor and the provision of a helical flange around the outside of the rotor. All of these constitute attempts to provide flow through the rheometer to prevent the build-up of solids on layers in the region of the rotor/stator but to date have not been particularly effective.

SUMMARY OF THE INVENTION

It is an object of the present invention to provide means for obviating or mitigating the effects outlined above, especially for the outer rotor/inner stator geometry (hereinafter called "Couette geometry") which is specified by the API as giving better results than the inner rotor/outer stator geometry (hereinafter called "Searle geometry").

The invention resides in the realization that the provision of a pulsatile flow is necessary to maintain particulate matter in suspension and provide flow through the rotor/stator arrangement In accordance with the present invention, there is provided a rheometer, comprising a cup for a fluid to be measured, a coaxial rotor and stator arrangement, and means for providing pulsatile, non-laminar flow of the fluid.

By providing a pulsatile, non-laminar flow, particulate matter can be maintained in suspension and flow induced through the measuring system thus ensuring that the fluid being measured corresponds as closely as possible to the fluid of interest, eg drilling mud, cement, etc. Furthermore, the flow can be maintained during measurement.

The term "pulsatile non-laminar flow" is used to indicate flow which could be oscillating without any net circulation of fluid in the system or a flow which is pulsating whilst circulating fluid and also to flow which might be considered as turbulent rather than laminar. It is the intention that the flow in the rheometer provides sufficient energy to the fluid in an appropriate manner to maintain any dispersed phase in suspension such that the fluid is substantially homogenous.

The invention applies equally to both Couette and Searle geometry rheometers, although Couette geometry is generally preferred. The rotor can typically be driven at any of a variety of constant speeds and the torque can be measured either at the rotor or the stator.

The means for providing pulsatile, non-laminar flow is typically a circuit connected to the cup and including a suitable pump.

The inlet and outlet for the pumping circuit are conveniently at or near the bottom of the cup so as to counteract the effect of gravity separation as much as possible. The pump preferably comprises an air driven diaphragm-type pump.

DESCRIPTION OF THE PREFERRED EMBODIMENT

The present invention will now be described with reference to the accompanying drawings, in which.

Figure 4:
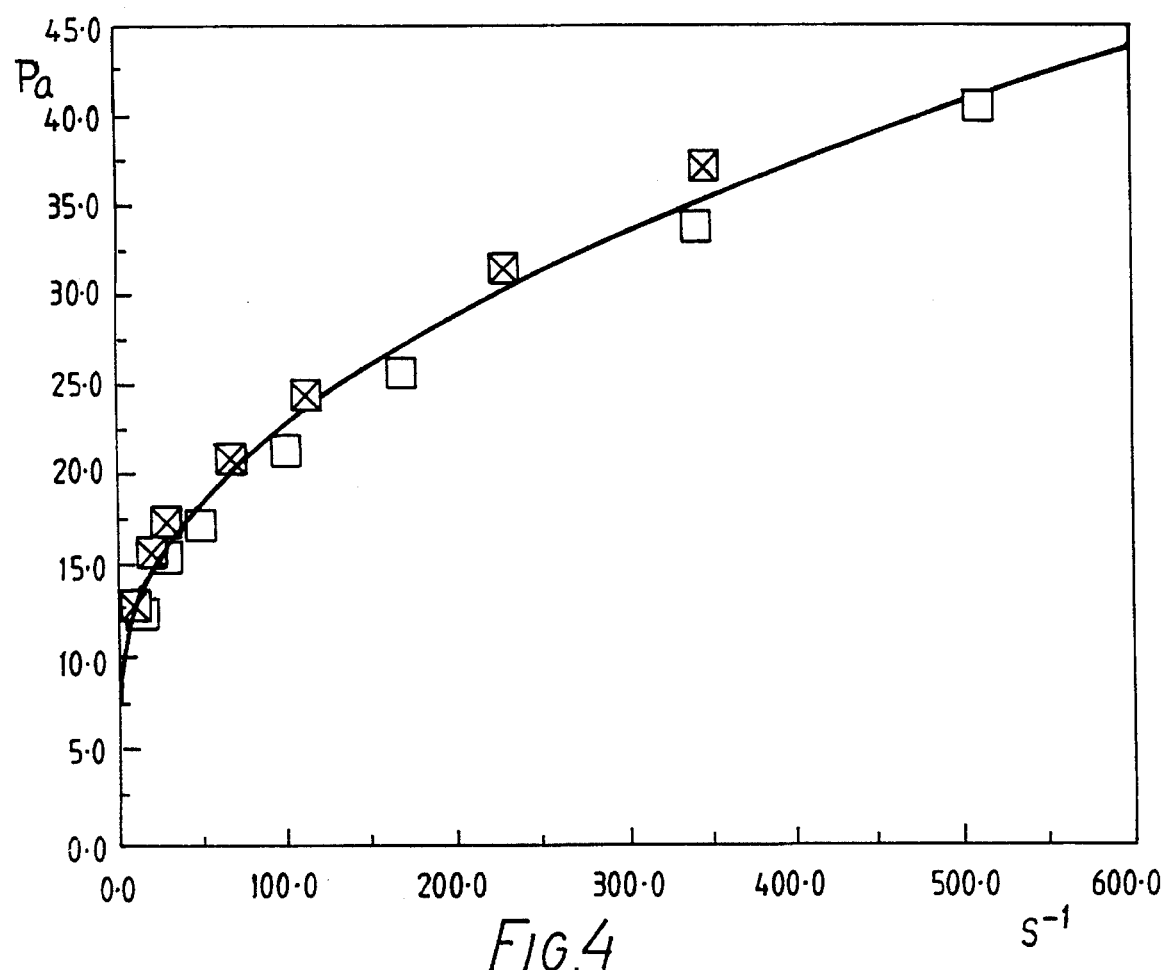
Figure 3A:
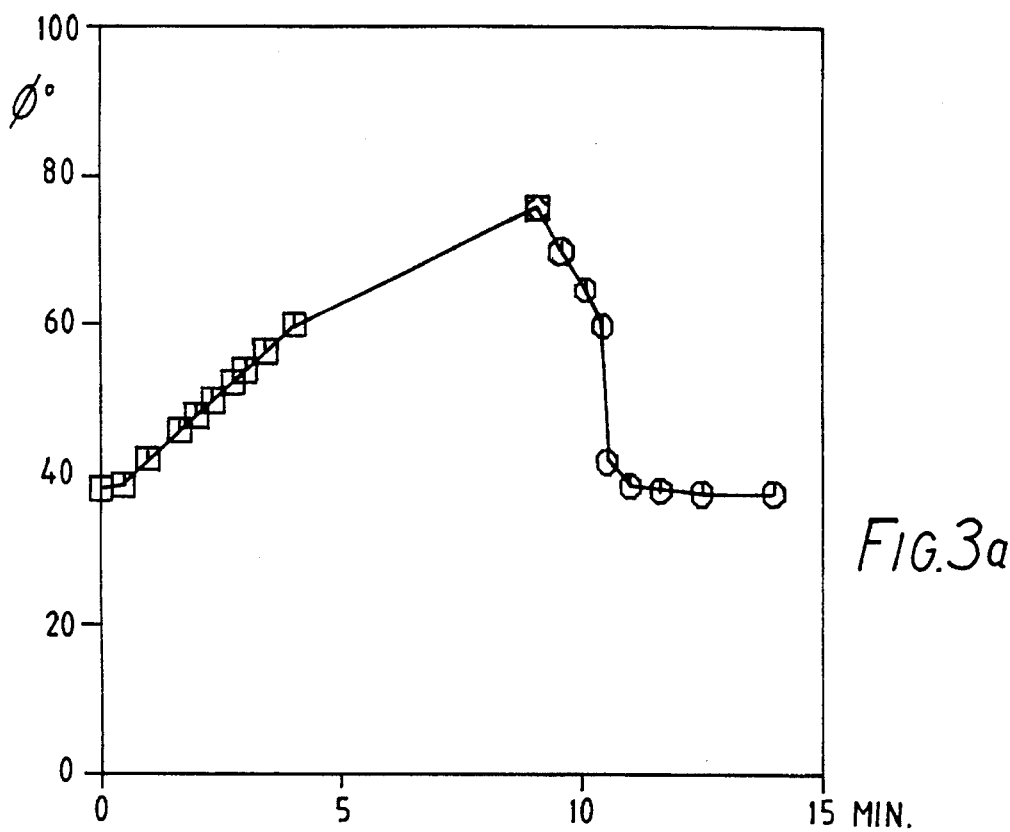
Figure 3B:
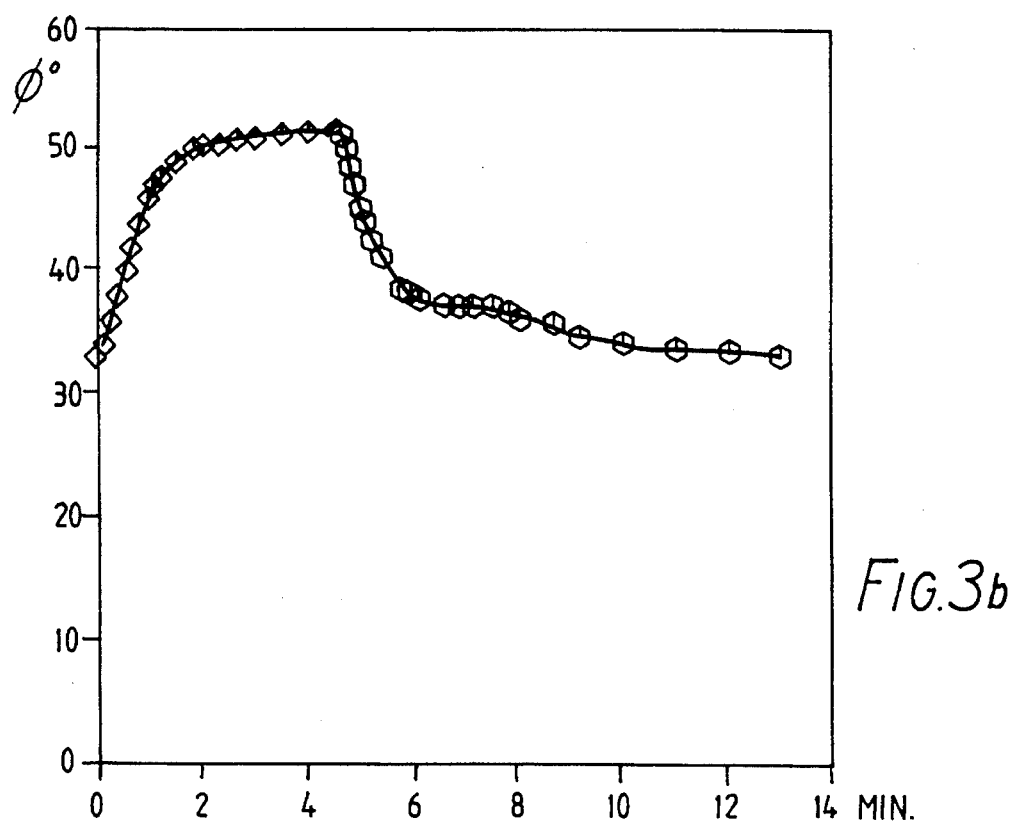
Figure 5:
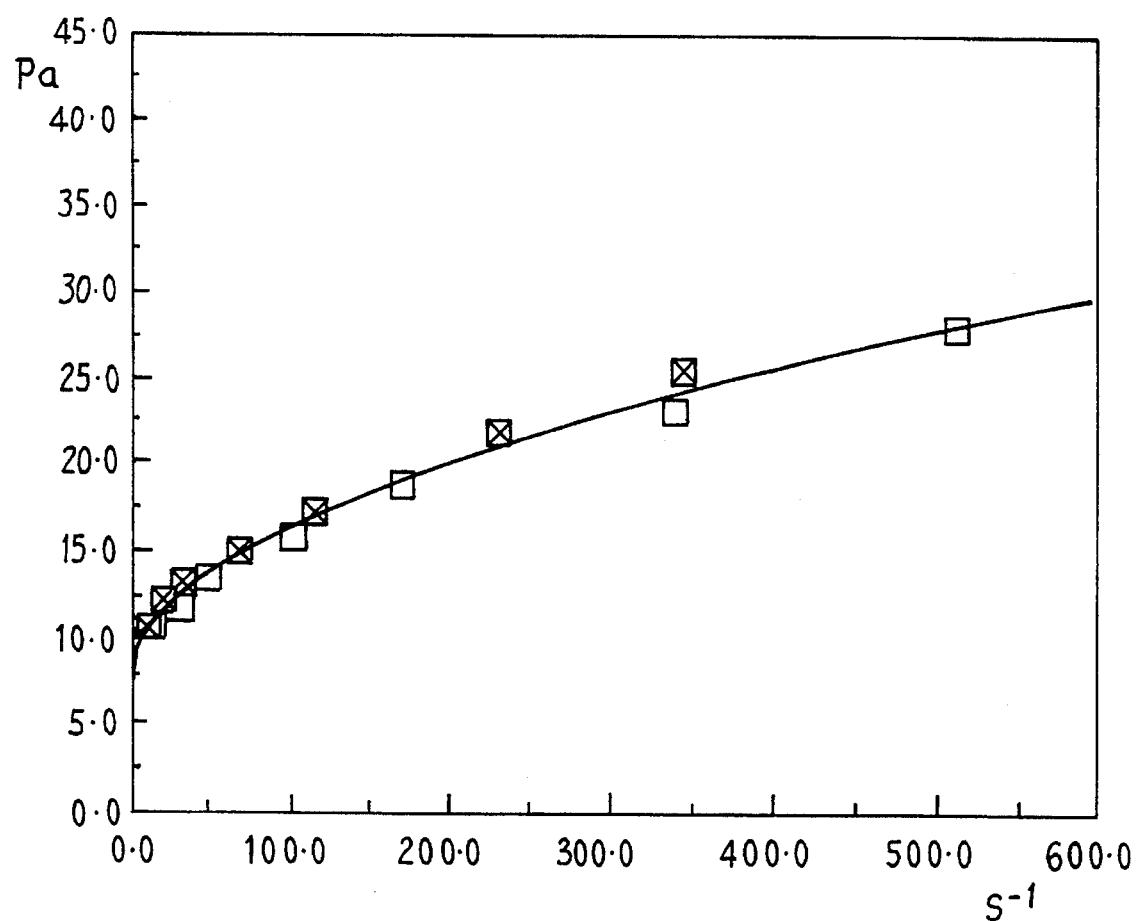
Figure 6:
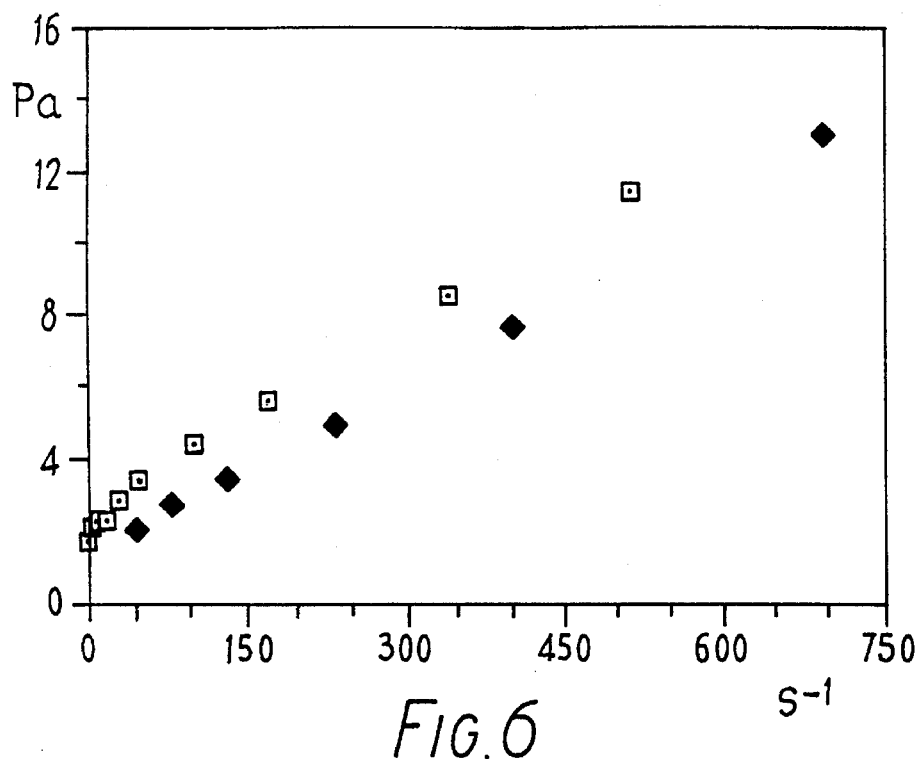
Figure 7:
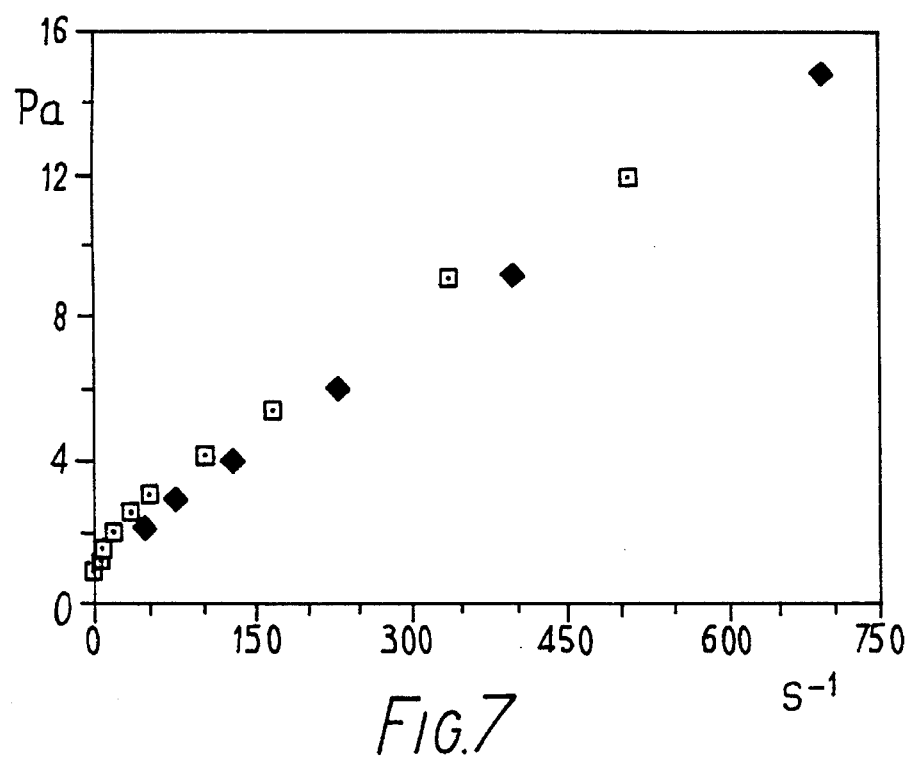

FIGS. 3(a) and 3(b) show a comparison of measurements (torque angledφ against time/min) on a mud and spacer respectively with and without pumping;

FIG. 4 shows a comparison of results (stress/Pa against rate/s$^{-1}$) using different rotor dimensions without pumping □=R1, ⊠=R1.5;

FIG. 5 shows the corresponding comparison to FIG. 4 with pumping;

FIG. 6 shows a comparison of readings (stress/Pa against shear rate/s$^{-1}$) between rheometers of Couette ▣ and Searle ● geometry without pumping;

FIG. 7 shows the corresponding comparison to FIG. 6 with pumping; and

Figure 8:
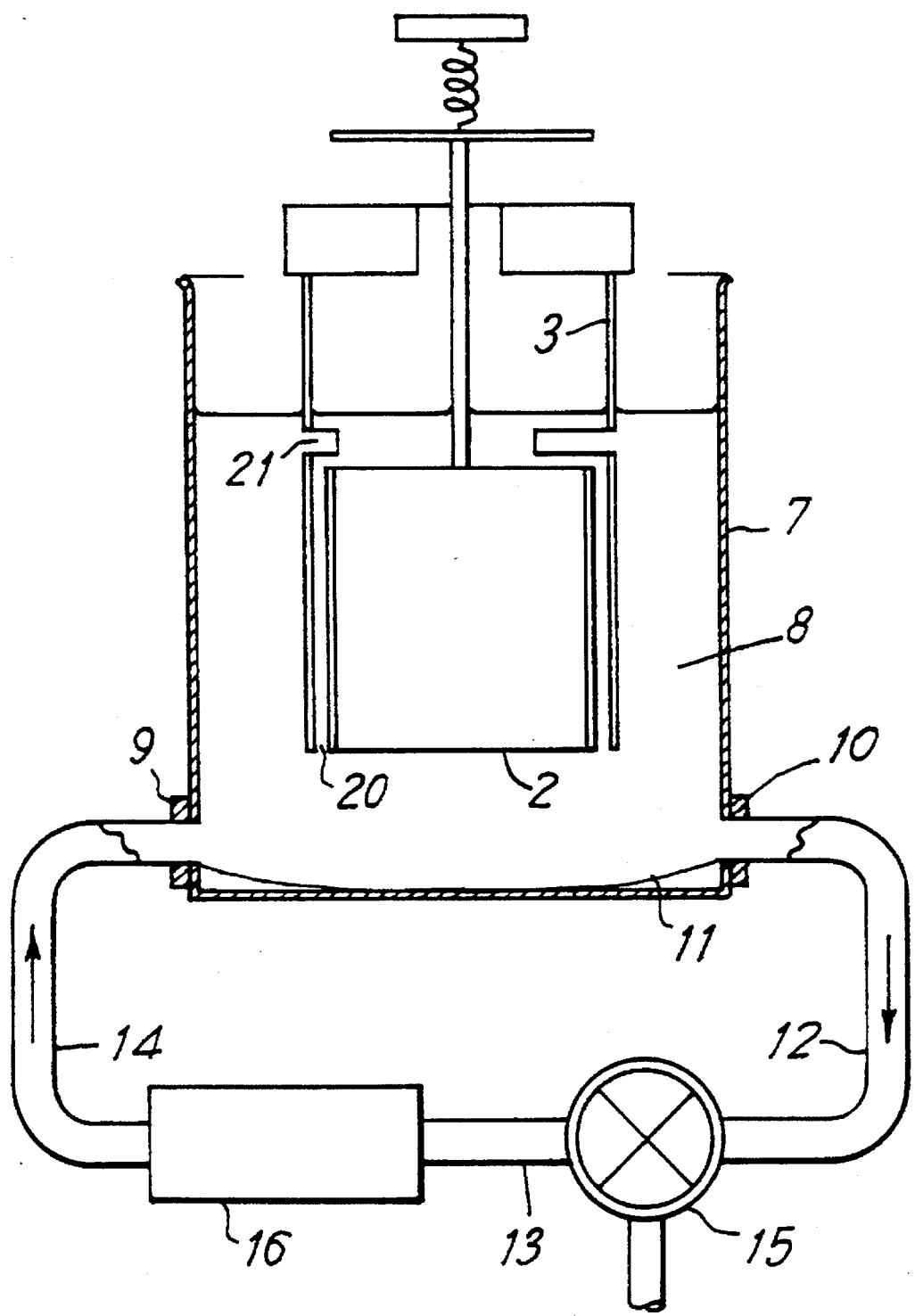

FIG. 8 shows an alternative embodiment of the invention using Searle geometry.

Figure 1:
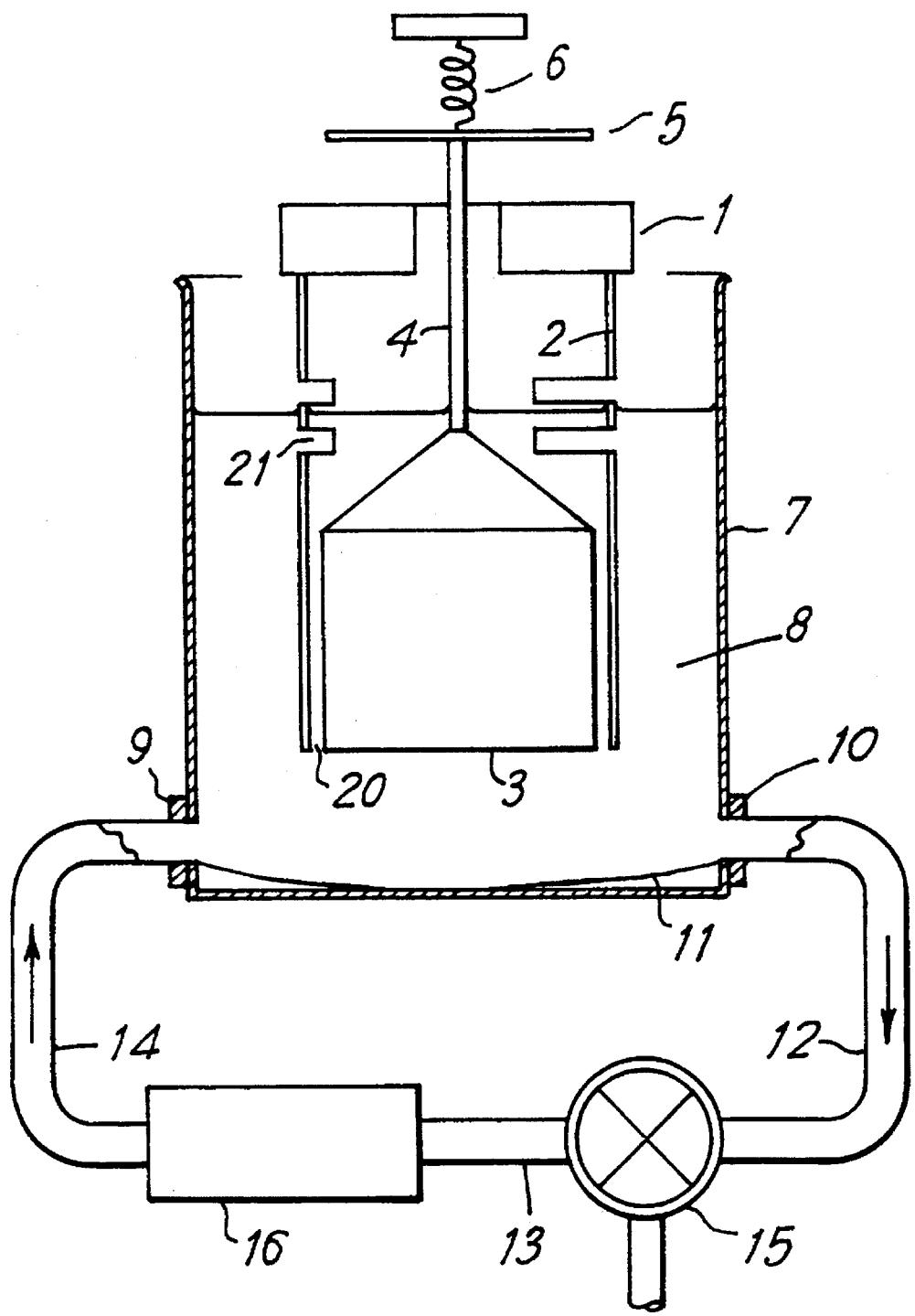
FIG. 1 shows a diagrammatic representation of one embodiment of the invention.

FIG. 1 shows a schematic diagram of a pumped-cup rheometer according to one embodiment of the invention. A Chan 35 (EG and G Chandler Engineering) model to API specification is used. The rotor boss 1 and rotor 2 impress a torque on the bob 3 through the fluid 8 under study. The torque is transmitted via shaft 4 to a rotary dial 5 and torque-string 6. The cup 7 holding fluid 8 has inlet and outlet holes 9, 10 on a cup diameter near the bottom thereof and has a dished bottom 11. Pipes 12, 13 and 14 of nominal ½" bore connect the inlet and outlet holes 9 and 10 to a pump 15 and stationary mixer 16. The pump is an air-driven diaphragm type (ARO ½") giving an unidirectional but pulsed flow of period typically 0.5 s. The pump volume flux is typically 0.1 L s$^{-1}$, controlled by the air pressure via an air regulator and oiler (not shown).

Two rotors 2 are used, the first is supplied with the Chan 35 and corresponds to the API R1 specification, giving an annular gap of 1.17 mm. The second is made from Perspex and has a larger internal diameter than the R1, giving ⅔ rd of the R1 shear rate for the same rotor speed. This we called the R1.5 rotor, and it gave an annular gap of 1.82 mm. The shear rate $\gamma$ at the bob wall is obtained from the rotor speed N using:

$$\dot{\gamma} = \frac{2b^2\omega}{b^2 - a^2}$$

where the angular speed of the rotor $$\omega/\text{rad } s^{-1} = \frac{2\pi}{60} \ (N/RPM)$$

and a and b are the radii of the bob and the rotor, respectively. Here $2a = 34.490$ mm for the bob 3, $2b = 36.830$ mm for the rotor R1 and $2b = 38.136$ mm for rotor R1.5.

The shear stress $\tau_a$ at the bob wall is obtained from the deflection $\theta_a$ on the scale 5 using:

$$\tau_a = k_1 k_2 \theta_a$$

where $k_1 k_2 = 0.511$ Pa deg$^{-1}$.

The pump 15 has two chambers which communicate with the compressed air via flexible diaphragms (not shown). The pump 15 acts by alternately filling and purging the cement slurry from the chambers. The effective volume V of each chamber was found to be 56 mL. The period T of the pump was that time taken to go from one state in one chamber to an identical state in the other. This is measured by means of a pressure-actuated switch (not shown), driven by the pressure pulse from the pump exhaust, which sends a voltage pulse to an electronic timer (not shown). Tests show that the pump pressure p in the pumped fluid slurry is less than the compressed air pressure (Pa) by about 0.3 bar owing to the rigidity of the diaphragms. Assuming the work done by the compressed air to be predominantly spent in the slurry, the dissipated power per kg of slurry, w, was obtained from:

$$w = \frac{pV}{mT}$$

where m was the mass of the circulating slurry.

In the experimental measurement described, the fluid slurry used is Cemoil G mixed to API specification 10, section 5, using a Waring blender at 4,000 RPM for 15 s and then at 12,000 RPM for 35 s. After mixing the slurry is made to a smooth consistency by rolling in a 4.5 L bottle on a Luckman Multimix roller at about 60 RPM for 20 min before use. The slurry thus treated is a smooth, homogeneous mix, apparently free from lumps or air bubbles. the composition to obtain 1 L of slurry is:

573 g water
0.3 g antifoaming agent D47
6.6 g retarder D28 (when required)
1316 g class G cement powder After rolling the slurry is immediately poured into the rheometer cup 7 with the pump 15 going slowly. When the pump 15, tubing 12, 13, 14 and cup 7 are full the cup 7 was offered to the rotor 2 and bob 3 for measurement. After prolonged use no sedimentary cement layer is apparent at the bottom of the cup 7, in contrast with the usual unpumped cup.

Figure 2:
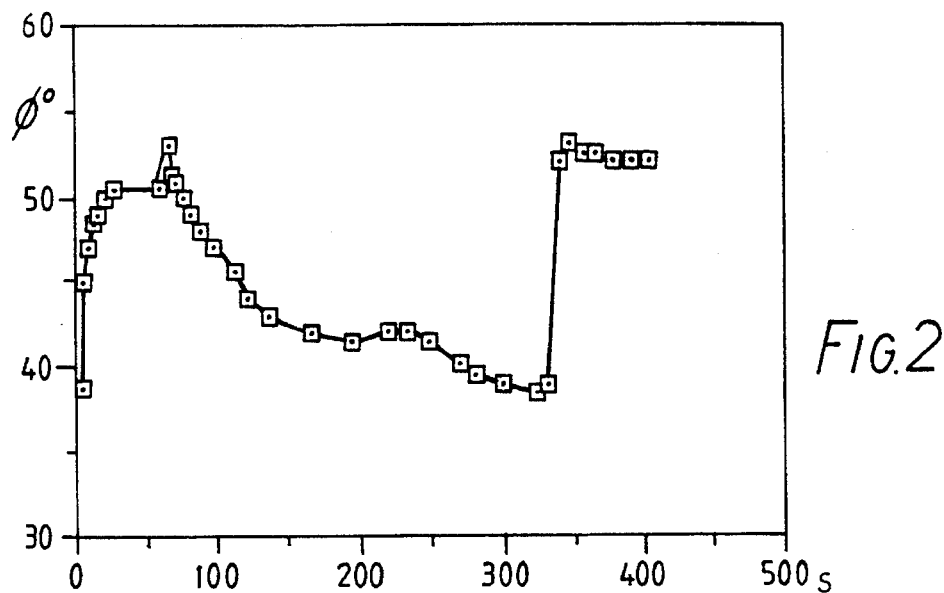
FIG. 2 shows a comparison of measurements (torque angle/φ against time/s) on a cement with and without pumping.

FIG. 2 shows the effect of measuring the torque at 600 RPM for an unretarded slurry. Without the pump it can be seen that the torque, as measured by $\theta_a$, is increasing with time. Even in the first 10 s, the torque increases by about 20%. The effect of the pump, after about 250 s, is shown to bring the torque back to its starting value. Stopping the pump at 330 s is shown to allow the torque to regain its high value within about 10 s.

A similar effect is found for weighted muds and weighted spacers. FIGS. 3(a) and 3(b) show the effect of the pump for a weighted waterbase mud of density about 1900 kg m$^{-3}$ running at 300 RPM and on a spacer weighted to about 1520 kg$^{-3}$ and running at 600 RPM. The similarity of behaviour shown by cement, mud and spacer suggests that the mechanism of the upward drift in torque is common to all granular materials in the Couette geometry and might originate from the centrifugally-driven radial migration of the denser grains. Whatever its true origin, the associated rheological error appears to be ameliorated by the use of the pumped cup.

If the true theology is being measured it should be independent of the magnitude of the annular gap. This is tested using unretarded slurry with the R1 and R1.5 rotors, with and without the pump. FIG. 4 shows the effect of using both rotors without the pump. The R1.5 rotor is seen to give a consistently greater apparent shear stress. The effect of using the pump in the same experiment is shown in FIG. 5. Although there is a slight tendency for the R1.5 rotor shear stress data to lie above the shear stress of the R1 rotor the dam sets are much closer than without the pump. Furthermore, within the experimental scatter on each data set, the agreement between then is acceptable.

FIGS. 6 and 7 show a comparison of Couette and Searle geometries, the Couette geometry being represented by the Chan 35 with the R1 rotor, while the Bohlin Visco 88 is used to provide an inner rotor (Searle) geometry. The Bohlin Visco 88 is a portable rheometer which has LCD readouts of the shear rate and shear stress and has an open-bottomed annular gap (similar to the Chan 35) to enable it to be dipped into the sample fluid. A diagramatic representation of the Searle geometry is shown in FIG. 8 with corresponding numerals to FIG. 1. The inner cylinder 2 rotates and senses the viscous torque, while the outer cylinder 3 is stationary and has large holes 21 in its wall above the level of the rotor top. A range of stators and rotors are available. A 30 mm diameter rotor and the 33 mm inside diameter stator is chosen, giving a gap of 1.5 mm compared with 38 mm of the API bob of the Chan 35. When used with the pump, the Bohlin Visco 88 stator and rotor assembly is dipped into the pumped cup as described above, such that the slurry can flow out of the large holes in the cylindrical walls of the stator.

FIG. 6 shows how the Couette and Searle geometries compare for unpumped, retarded Cemoil G Slurry. A considerable disagreement is evident, which is largely resolved when the pump is used as shown by the data in FIG. 7. Again, the use of the pump seems to enable a close theological accord between the two different measurement geometries, suggesting that the true cement theology is being measured if the pump is used.

To interpret the data obtained from the rheometer measurements, the results are compared with rheology models such as the Herschel-Bulkley model $$\tau = \tau_y + k\gamma^n,$$

and the Robertson-Stiff model $$\tau = (\tau_y^{1/m} + K\gamma)^m$$

Both functions are found to fit the data equally well. A difference between them is their behaviour as $\gamma \to 0$. Whereas $d\tau/d\gamma \to \infty$ for the Herschel-Bulkley model, the Robertson-Stiff model gives $d\tau/d\gamma = mK\tau^{1-m^{-1}}$ which remains finite. While the Herschel-Bulkley and Robertson-Stiff models have been found appropriate, there may be situations where other models such as Ostwald-de Wade or Bingham which may be more appropriate in certain circumstances.

Using the procedure outlined above for obtaining good cement slurry rheology measurements the effect of varying the pumping power can be studied. The pump is run at a range of speeds and the Herschel-Bulkley parameters were measured at each pump speed. The slurry temperature rises by about 3° C. during this experiment but preliminary experiments show that such temperature changes do not have a major effect. The effect of pump power on the Herschel-Bulkley parameters is not believed to be large and may be regarded as negligible. Thus we regard this particular slurry as being practically non-thixotropic.

It is understood that one explanation for the operation of the pumped cup is that fluid is drawn down the annular gap 20 by the shedding of eddies. This refreshes the fluid being measured in the annular gap with fluid drawn through the holes 21 in the top of the rotor. This fluid is turbulent and kept continually refreshed by well-mixed fluid entering the cup from the stationary mixer. Thus the overall effect of the pulsatile flow is to irrigate the annular gap with well-mixed fluid at the expected concentration of particles and neither enriched nor depleted by the processes of sedimentation and centrifugation, and make the fluid homogenised before it enters the annular gap. The pumped cup may thus provide an alternative to the rheometer and consistometer presently recommended by the API for other cement measurements.

I claim:

1. A rheometer for measuring the rheological characteristics of a fluid comprising:
    a) a cup for holding the fluid to be measured, the cup having in use an upper and a lower portion;
    b) a coaxial rotor and stator arrangement positionable within the upper portion of the cup;
    c) means for driving the rotor;
    d) means for sensing and measuring the torque effect caused by the fluid; and
    e) means for providing a non-laminar and pulsatile flow of fluid through the cup while the torque effect is sensed and measured.

2. A rheometer as claimed in claim 1, wherein there are inlet and outlet ports in the lower part of the cup, and the pipe circuit is connected to the cup via these inlet and outlet ports.

3. A rheometer as claimed in claim 1, wherein the stator is located within the rotor.

4. A rheometer as claimed in claim 1 wherein the means for sensing and measuring the torque effect comprises means for sensing and measuring the torque acting on the stator.

5. A rheometer as claimed in claim 1, wherein the pump means is a diaphragm pump with a controllable throughput rate.

6. A rheometer for measuring the rheological characteristics of a fluid comprising a dispersed particulate phase suspended in a continuous liquid phase, comprising:
    a) a cup, having an upper and a lower portion, for holding the fluid to be measured;
    b) a coaxial rotor and stator arrangement positionable within the upper portion of the cup;
    c) means for driving the rotor;
    e) means for circulating a pulsatile flow of the fluid through the cup; and
    d) means for sensing and measuring, during circulation, the torque effect between the rotor and stator caused by the presence of the fluid.

7. A rheometer according to claim 6, wherein the means for circulating imparts sufficient energy to the fluid to maintain substantially all of the dispersed phase in suspension in the cup during measurement.

8. A rheometer according to claim 6, wherein the means for circulating imparts sufficient energy to the fluid to maintain the particulate phase as a substantially homogenous dispersion in the cup during measurement.

9. A rheometer according to claim 6, wherein the means for circulating causes a flow of the fluid in the cup which prevents the build-up of solids in the lower portion of the cup during measurement.

10. A method of determining the rheological characteristics of a fluid comprising a dispersed particulate phase suspended in a continuous liquid phase, the method comprising:
    a) using a rheometer comprising a cup, having an upper and a lower portion, for holding the fluid to be measured, a coaxial rotor and stator arrangement positionable within the upper portion of the cup, means for driving the rotor, means for circulating a pulsatile flow of the fluid through the cup, and means for sensing and measuring, during circulation, the torque effect between the rotor and stator caused by the presence of the fluid;
    b) circulating the fluid through the cup using the circulating means;
    c) measuring the torque effect of the fluid during circulation; and
    d) determining the rheological properties of the fluid from the measurement of torque effect.

11. A method according to claim 10, wherein the step of circulating comprises imparting sufficient energy to the fluid to maintain substantially all of the dispersed phase in suspension in the cup during measurement.

12. A method according to claim 10, wherein the step of circulating comprises imparting sufficient energy to the fluid to maintain the particulate phase as a substantially homogenous dispersion in the cup during measurement.

13. A method according to claim 10, wherein the step of circulating comprises causing a flow of the fluid in the cup which prevents the build-up of solids in the lower portion of the cup during measurement.

* * * * *